(12) United States Patent
Anderson et al.

(10) Patent No.: US 6,258,854 B1
(45) Date of Patent: Jul. 10, 2001

(54) KETONE PRECURSORS FOR ORGANOLEPTIC COMPOUNDS

(75) Inventors: Denise Anderson, Zürich; Georg Fráter, Winterthur, both of (CH)

(73) Assignee: Givaudan Roure (International) SA, Vernier, Geneva (CH)

( * ) Notice: Subject to any disclaimer, the term of this patent is extended or adjusted under 35 U.S.C. 154(b) by 0 days.

(21) Appl. No.: 09/387,980

(22) Filed: Sep. 1, 1999

(30) Foreign Application Priority Data

Sep. 4, 1998 (EP) .................................................. 98810883

(51) Int. Cl.$^7$ ........................... A61K 31/12; A61K 7/46; C07C 49/303
(52) U.S. Cl. ........................ 514/688; 514/678; 514/679; 514/690; 512/10; 568/308; 568/325; 568/328; 568/329; 568/331
(58) Field of Search ..................... 568/308, 309, 568/338, 382, 383, 331, 325, 328, 329; 560/129; 562/512; 512/10; 514/678, 679, 688, 690

(56) References Cited

U.S. PATENT DOCUMENTS

| | | | |
|---|---|---|---|
| 4,108,880 | 8/1978 | Gander et al. | 260/410.5 |
| 5,128,749 | 7/1992 | Hornback et al. | 357/80 |
| 5,214,027 | 5/1993 | Ishihara et al. | 512/10 |
| 5,726,345 | 3/1998 | Paget et al. | 560/238 |

FOREIGN PATENT DOCUMENTS

| | | |
|---|---|---|
| EP 700 896 | 3/1996 | (EP) . |
| EP 709 382 | 5/1996 | (EP) . |
| EP 776 881 | 6/1997 | (EP) . |
| 0816 322 | 2/1998 | (EP) . |
| GB 1 488 061 | 10/1977 | (GB) . |
| WO 90/06751 | 6/1990 | (WO) . |
| WO 94/06748 | 3/1994 | (WO) . |
| WO 95/04809 | 2/1995 | (WO) . |
| WO 97/29100 | 2/1997 | (WO) . |
| WO 98/07405 | 2/1998 | (WO) . |

OTHER PUBLICATIONS

Indian J. Chem., Sect. B, 14B (8), pp. 606–608 (Abstract Attached to Office Artum), 1976.
J.Med.Chem., 16(9), pp. 1020–2 (Abstract Attached to Office Artum), 1973.
Chemical Abstracts, 127(16), 220571 (1997).
Chemical Abstracts, 127(7), 95089 (1997).
Chemical Abstracts, 125(6), 67715 (1996).
Chemical Abstracts, 124(22), 298449 (1996).
Chemical Abstracts, 122(26), 322622 (1995).
Chemical Abstracts, 121, 308502 (1994).
Chemical Abstracts, 121(7), 82745 (1994).
Chemical Abstracts, 121(9). 108705 (1994).
Chemical Abstracts, 114(11), 101370 (1991).
Chemical Abstracts, 110(6), 44738 (1989).
Chemical Abstracts, 104(24), 213002 (1986).
Chemical Abstracts, 96(23), 199264 (1982).
Chemical Abstracts, 88(13),89892 (1978).
Chemical Abstracts, 85, 46367 (1976).
Chemical Abstracts, 79, 137469 (1973).
Chemical Abstracts, 73(16), 98561 (1970).
Gatti, R., et al., *J Pharm. Biomed, Anal.*, 13(4/5). 589–95 (1995).
Ferioli, V., et al., *Il Farmaco*, 49(6), 421–425 (1994).
Narvaez, J.N., et al., *Chemical Senses*, 11(1), 145–156 (1986).
Sheehan, J. C., et al., *J. Org.Chem.*, 38(21),3771–4 (1973).
Tsai, P., et al., *J. Food Science & Tech.*, 16(8),346–9 (1969).
Chemical Abstracts, 108(3), 021462 (1988).
Kulka, K., et al., *Perfumer & Flavorist*, (3) 39–42, (1978).
Kovach, I.M., et al., *J. Am. Chem. Soc.*, 115(23) 10471–10476, (1993).
Langenbeck, W., et al., *Chem. Ber.*, 69(3) 514–516, (1936).
Wilbur, D.S., *J. Org. Chem.*, (48) 1542–1544, (1983).

Primary Examiner—Sreeni Padmanabhan
(74) *Attorney, Agent, or Firm*—Mark E. Waddell; Stephen M. Haracz; Bryan Cave LLP

(57) ABSTRACT

The invention discloses ketones of formula I:

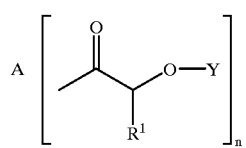

wherein,
Y is an optionally substituted alkyl, cycloalkyl, or cycloalkylalkyl, wherein each alkyl group is straight or branched and each alkyl and cycloalkyl group is saturated or unsaturated;
$R^1$ is hydrogen or a $C_{1-6}$ alkyl group that is substituted, saturated or unsaturated, straight or branched;
A is a chromophoric substituted aromatic ring or ring system;
n is an integer; and
with the proviso that formula I is not 2-ethoxy-1-phenyl-ethanone. These compositions are useful for the delivery of organoleptic compounds, especially of flavors, fragrances, masking agents and antimicrobial compounds.

25 Claims, No Drawings

KETONE PRECURSORS FOR ORGANOLEPTIC COMPOUNDS

FIELD OF THE INVENTION

The present invention relates to new ketones. These ketones are useful as precursors for organoleptic compounds, especially fragrances and masking agents, and antimicrobial compounds.

BACKGROUND OF THE INVENTION

A principal strategy currently employed for imparting odors to consumer products is the admixing of a fragrance directly into the product. There are, however, several drawbacks to this strategy. The fragrance material may be too volatile and/or too soluble, resulting in fragrance loss during manufacturing, storage, and use. Many fragrance materials are also unstable over time. This again results in fragrance loss during storage.

In many consumer products, it is desirable for the fragrance to be released slowly over time. Microencapsulation and inclusion complexes with cyclodextrins have been used to help decrease volatility, improve stability, and provide slow-release properties. These methods, however, are for a number of reasons often not successful. In addition, cyclodextrins may be too expensive.

Fragrance precursors for scenting fabrics washed in the presence of a lipase-containing detergent are described in WO 95/04809. The fragrance precursors contained in a detergent and/or in a fabric softener are cleaved by the lipase and a single odoriferous compound (either an odoriferous alcohol or ketone) is formed. In this way, a prolonged scenting effect on the fabric is obtained.

EP-A-0 816 322 discloses fragrance precursor compositions containing carbonic acid esters or thiocarbonic acid esters. These compositions are used in cosmetic products or in laundry products. Such precursors produce fragrances upon contacting the skin or when used in the presence of lipases (e.g., such as those lipases used in detergents) thus providing a prolongation of the fabric scenting effect.

One object of the present invention is to provide new precursors for compounds with different activities.

A further object of the invention is to provide new compounds which are stable in a variety of applications including detergents, fabric softeners, cleaning products, personal care products, cosmetics, and sun protection products.

A further object of the invention is to provide new compounds that may be cleaved by light, heat, hydrolysis, and/or enzymes into one or more organoleptic compounds.

SUMMARY OF THE INVENTION

One embodiment of the present invention is a ketone of the formula I:

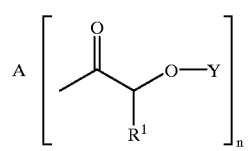

I wherein

Y is an optionally substituted alkyl, cycloalkyl, cycloalkylalkyl, alkylcarbonyl, cycloalkylcarbonyl, arylcarbonyl, alkyloxycarbonyl, cycloalkyloxycarbonyl, aryloxycarbonyl, amide, oximinocarbonyl, alkylthiocarbonyl, cycloalkylthiocarbonyl, wherein each alkyl group is straight or branched and each alkyl and cycloalkyl group is saturated or unsaturated;

$R^1$ is hydrogen or a $C_{1-6}$ alkyl group that is substituted, saturated or unsaturated, straight or branched;

A is a chromophoric aromatic or heteroaromatic ring or ring system, and carries 1 to 8 substituents selected from the group consisting of hydrogen, hydroxy, mercapto, amino, acyl, ester, esterified hydroxy group, cyano, nitro; substituted, saturated or unsaturated, straight or branched alkyl, alkoxy, alkylthio, and arylalkoxy groups; substituted or unsubstituted aryl and heteroaryl groups, and a polymeric group;

n is an integer; and with the proviso that formula I is not 2-ethoxy-1-phenyl-ethanone, hydroxy-acetic acid 2-oxo-2-phenyl-ethyl ester, acetic acid 1-methyl-2-oxo-2-phenyl-ethyl ester, or p-methoxyphenacyl acetate.

Another embodiment of the invention is a precursor of an active compound that includes a ketone of the formula I:

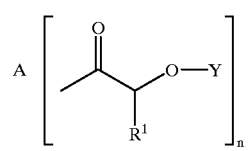

I wherein

Y is an optionally substituted alkyl, cycloalkyl, cycloalkylalkyl, alkylcarbonyl, cycloalkylcarbonyl, arylcarbonyl, alkyloxycarbonyl, cycloalkyloxycarbonyl, aryloxycarbonyl, amide, oximinocarbonyl, alkylthiocarbonyl, cycloalkylthiocarbonyl, wherein each alkyl group may be straight or branched and each alkyl and cycloalkyl group may be saturated or unsaturated;

$R^1$ is hydrogen or a $C_{1-6}$ alkyl group that may be substituted, saturated or unsaturated, straight or branched;

A is a chromophoric aromatic or heteroaromatic ring or ring system, and A carries 1 to 8 substituents selected from the group consisting of hydrogen, hydroxy, mercapto, amino, acyl, ester, esterified hydroxy group, cyano, nitro; substituted, saturated or unsaturated, straight or branched alkyl, alkoxy, alkylthio and arylalkoxy groups; substituted or unsubstituted aryl and heteroaryl groups, and a polymeric group; and n is an integer.

Another embodiment is a composition selected from detergents, fabric softeners, personal care products, cleaning compositions, cosmetics, and sun protection products in admixture with the precursor defined above.

Another embodiment is a method of imparting a sustained release odorant and/or an antimicrobial agent into a consumer product that includes mixing the consumer product with at least one compound according to formula I:

$$\text{A} \left[ \begin{array}{c} \text{O} \\ \| \\ \text{C} - \text{CH} - \text{O} - \text{Y} \\ | \\ \text{R}^1 \end{array} \right]_n \quad \text{I}$$

wherein

Y is an optionally substituted alkyl, cycloalkyl, cycloalkylalkyl, alkylcarbonyl, cycloalkylcarbonyl, arylcarbonyl, alkyloxycarbonyl, cycloalkyloxycarbonyl, aryloxycarbonyl, amide, oximinocarbonyl, alkylthiocarbonyl, cycloalkylthiocarbonyl, wherein each alkyl group is straight or branched and each alkyl and cycloalkyl group is saturated or unsaturated;

$R^1$ is hydrogen or a $C_{1-6}$ alkyl group that is substituted, saturated or unsaturated, straight or branched;

A is a chromophoric aromatic or heteroaromatic ring or ring system, and carries 1 to 8 substituents selected from the group consisting of hydrogen, hydroxy, mercapto, amino, acyl, ester, esterified hydroxy group, cyano, nitro; substituted, saturated or unsaturated, straight or branched alkyl, alkoxy, alkylthio, and arylalkoxy groups; substituted or unsubstituted aryl and heteroaryl groups, and a polymeric group;

n is an integer; and with the proviso that formula I is not 2-ethoxy-1-phenyl-ethanone, hydroxy-acetic acid 2-oxo-2-phenyl-ethyl ester, acetic acid 1-methyl-2-oxo-2-phenyl-ethyl ester, or p-methoxyphenacyl acetate.

In this method, the consumer product is selected from laundry detergents, fabric softeners, fabric softener sheets, cleaning compositions, swimming pool additives, toiletries, and cosmetic products, such as shampoo, conditioners and sunscreens.

In this embodiment, the precursor is activated to form an organoleptic and/or antimicrobial agent. The precursor is activated by exposure to an activating agent selected from the group of light, heat, hydrolysis, and enzymes.

DETAILED DESCRIPTION OF THE INVENTION

The present invention discloses new ketones of the formula I:

$$\text{A} \left[ \begin{array}{c} \text{O} \\ \| \\ \text{C} - \text{CH} - \text{O} - \text{Y} \\ | \\ \text{R}^1 \end{array} \right]_n \quad \text{I}$$

wherein

Y is an optionally substituted alkyl, cycloalkyl, cycloalkylalkyl, alkylcarbonyl, cycloalkylcarbonyl, arylcarbonyl, alkyloxycarbonyl, cycloalkyloxycarbonyl, aryloxycarbonyl, amide, oximinocarbonyl, alkylthiocarbonyl, cycloalkylthiocarbonyl, wherein each alkyl group may be straight or branched and each alkyl and cycloalkyl group may be saturated or unsaturated;

$R^1$ is hydrogen or a $C_{1-6}$ alkyl group that may be substituted, saturated or unsaturated, straight or branched;

A is a chromophoric aromatic or heteroaromatic ring or ring system having 1 to 8 substituents selected from hydrogen, hydroxy, mercapto, amino, acyl, ester, esterified hydroxy group, cyano and nitro; substituted, saturated or unsaturated, straight or branched alkyl, alkoxy, alkylthio and arylalkoxy groups; substituted or unsubstituted aryl and heteroaryl, and a polymeric group;

n is an integer; and with the proviso that formula I is not 2-ethoxy-1-phenyl-ethanone, hydroxy-acetic acid 2-oxo-2-phenyl-ethyl ester, acetic acid 1-methyl-2-oxo-2-phenyl-ethyl ester, or p-methoxyphenacyl acetate.

As used herein, each group containing the term "alkyl" includes the unsaturated residues thereof, e.g. alkenyl, alkynyl, cycloalkenyl, etc.

In the present invention, the compounds of formula I are not limited to any particular stereoisomers. Accordingly, all possible stereoisomers (E/Z isomers, enantiomers, diastereomers) and mixtures thereof are included within the scope of the invention.

The compounds of formula I are odorless or nearly odorless at room temperature, atmospheric conditions, and about 20% to 100% relative humidity. Under activating conditions, these compounds are cleaved and form one or more active compounds with organoleptic properties.

The compounds of formula I may be activated under a variety of conditions which lead to cleavage of the formula I compound and formation of the desired active compound (s). For example, actinic radiation, such as room light or sunlight, may activate the present compounds. In the present invention, sunlight is preferred. Additional activating conditions include heat, hydrolysis, and/or exposure of the compounds of formula I to enzymes.

After cleavage, the compounds of formula I form an aryl or heteroaryl ketone of the formula II:

$$\text{A} \begin{array}{c} \text{O} \\ \| \\ \text{C} - \text{CH}_2 - \text{R}^1 \end{array} \quad \text{II}$$

wherein A and $R^1$ are defined as set forth above.

Preferred compounds of formula I are those which form an organoleptic aryl ketone.

In formula I, when Y is an alkyl, cycloalkyl or cycloalkylalkyl group, the compound may be cleaved into an aryl or heteroaryl ketone and an aldehyde or ketone, at least one of which is organoleptic. Examples of organoleptic aryl ketones, ketones, and aldehydes are set forth below.

Examples of organoleptic heteroaryl ketones include 2-acetylpyrazine, 2-acetyl-3-methylpyrazine, 2-acetyl-5-ethylpyrazine, 2-acetylpyridine, and the acetylpyridines which are disclosed in U.S. Pat. No. 5,214,027 to Ishihara, et al., which is hereby incorporated by reference as if cited in full herein.

In formula I, when Y is an alkyl-, cycloalkyl- or aryloxy-carbonyl group, the compound may be cleaved into an aryl or heteroaryl ketone and an alcohol, phenol, aldehyde or ketone, at least one of which is organoleptic. Examples of alcohols and phenols that are formed from cleavage of a compound of formula I are also set forth below.

As used herein, the term "phenol" is intended to mean an aromatic hydroxy compound wherein the hydroxy group is attached directly to a benzene ring.

In formula I, when Y is an alkyl-, cycloalkyl- or arylcarbonyl group, the compound may be cleaved to form an aryl or heteroaryl ketone and an acid or a lactone. The aryl or heteroaryl ketone and/or the lactone formed by the cleavage are organoleptic. When the alkyl residue of the alkylcarbonyl group is substituted in the alpha- or the beta-position with a hydroxy group, the released acid may be active as a peeling ingredient in cosmetics.

Lactones may be formed when the alkyl residue is substituted in the gamma- or the delta-position with a hydroxy group, a O—CO—OR$^2$ group or a O—CO—R$^2$ group, wherein R$^2$ is an alkyl, aryl or aralkyl group that may be branched, unsaturated and/or substituted. Preferred compounds are those wherein R$^2$ is a C$_{1\text{-}30}$ alkyl group or a phenyl C$_{1\text{-}10}$ alkyl group. Compounds of formula I with the O—CO—OR$^2$ group after cleavage form, besides the aryl or heteroaryl ketone and lactone, an alcohol, phenol, aldehyde or ketone. These three compounds may be organoleptic.

In formula I, when Y is an alkylcarbonyl group, the alkyl group may be substituted with, e.g., an oxo group. After cleavage, these compounds form an aryl or heteroaryl ketone and a ketone, at least one of which is organoleptic. Preferably, the alkyl group is substituted with an oxo group in the beta- or delta-position to the carbonyl group. In the latter case, the oxo group may be situated in an optionally unsaturated cycloalkyl radical that may be substituted.

When Y is an amide, i.e. an N-substituted aminocarbonyl group, the compounds of formula I are cleaved into an aryl or a heteroaryl ketone and an amine, at least one of which is organoleptic. Examples of organoleptic amines are listed below.

When Y is an alkylthiocarbonyl or cycloalkylthiocarbonyl group, the compounds of formula I are cleaved into an aryl or heteroaryl ketone and a thiol, at least one of which is organoleptic. Examples of organoleptic thiols are 3,7-dimethyl-1-thio-octa-2,6-diene, 2-(1-mercapto-1-methylethyl)-5-methylcyclohexanone, and 2-methoxy-2-methyl-butan2-thiol.

When Y is an oximinocarbonyl group, i.e. —CO—O—N=CR$^3$R$^4$, wherein R$^3$ and R$^4$ are, for example, an optionally substituted, straight or branched, saturated or unsaturated alkyl group, the compounds of formula I, are cleaved to form an aryl or heteroaryl ketone and an oxime, at least one of which is organoleptic.

The present invention also includes compounds of formula I that are cleaved into an optionally organoleptic aryl or heteroaryl ketone and an organoleptic nitrile. In this case, Y is an alkyl- or alkenylcarbonyl group which is substituted with a cyano group in the alpha- and/or the gamma-position to the carbonyl group, with the proviso that the carbon chain between the carbonyl group and the cyano group has a double bond in a beta-gamma-position to the carbonyl group when the cyano group is in the gamma-position. The alkyl or alkenyl group may be branched and/or substituted with further residues that may together form a ring system. Examples of organoleptic nitriles according to the present invention are listed below.

In the compounds of formula I, A is a chromophoric aromatic or heteroaromatic ring or ring system. As used herein, the term "ring system" includes mono- and polycyclic rings, that may be connected either directly or by a bridge, e.g. an optionally unsaturated alkylene group, oxygen etc., as well as fused rings. As used herein, "heteroaromatic rings" include five- and six-membered rings.

In the present invention, A may be a ring system of the formula:

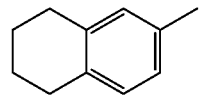

IV or

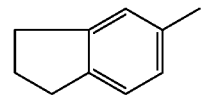

V in which both rings may be substituted.

In most cases, the obtained aryl or heteroaryl ketone is organoleptic. When one of the substituents of A represents a polymeric group or when A represents a fused aromatic or heteroaromatic ring system with more than two rings, the compounds of formula I release, upon cleavage, a non-organoleptic aryl or heteroaryl ketone. In these cases, O—Y in formula I represents a group, which after cleavage, forms at least one of an organoleptic aldehyde, an organoleptic ketone, an organoleptic alcohol or phenol, an organoleptic lactone, an organoleptic amine, an organoleptic thiol, an organoleptic oxime or an organoleptic nitrile, as described above.

In the present invention, the polymeric groups that may be used include divinylbenzene-based polymers, ethyleneglycol dimethacrylate-based polymers, acrylic acid/maleic acid copolymers, acrylic acid homopolymers, polysiloxanes, alginic acid, carboxymethyl cellulose, xanthan gum, and the like.

As set forth above, the compounds of formula I, after cleavage, form at least one of the following groups: aryl or heteroaryl ketones, aldehydes, ketones, alcohols, phenols, amines, thiols, oximes, nitrites, and lactones having organoleptic activity. Accordingly, these compounds allow the development of useful consumer products having enhanced organoleptic properties. The obtained organoleptic substances are useful as fragrances, masking agents, and antimicrobial agents.

Accordingly, the present invention also includes methods of making and using all of the compounds of formula I as precursors for, e.g., organoleptic compounds, in particular fragrances.

The compounds of formula I may act as fragrance precursors in a number of consumer products, including for example, laundry products, such as detergents and fabric softeners;

cleaning compositions, such as hard surface and all-purpose cleaners; personal care products, cosmetics or sun protection products. They may also act as precursors for odor masking agents in the same products as the fragrance precursors. The compounds of formula I may also act as precursors for antimicrobial agents. The fragrance precursors and the precursors for odor masking agents may be used individually in an amount effective to enhance or to mask the characteristic odor of a material. More commonly, the compounds are mixed with other fragrance components in an amount sufficient to provide the desired odor characteristics.

Due to the in situ generation of the active compounds, the desired (i.e., organoleptic and/or antimicrobial) effect is prolonged and the substantivity on different substrates is enhanced. If two or more active compounds are generated from a compound of formula I, they may be generated, depending on the precursor, simultaneously or successively. Further, the precursors of the invention may also provide slow release of the active compounds.

A preferred group of formula I ketones are those in which Y is an alkyl group. The alkyl group may contain a $C_{1-30}$ alkyl moiety, which may be unsaturated, branched and/or substituted by different groups as shown in the aldehydes and ketones set forth below.

Preferably, compounds of formula I are those in which A is one aromatic ring and two of its substituents form a second ring, preferably a six-membered aromatic ring or a five- or six-membered aliphatic ring. Within this group of compounds, it is preferred that $R^1$ is hydrogen and that the other substituents of the aromatic ring are hydrogen or one or more methyl groups.

Preferred compounds of formula I are also those wherein $R^1$ is hydrogen or methyl. Preferably, A has no more than three substituents. Preferably, the substituents are methyl groups.

A further preferred group of compounds of formula I are those wherein $R^1$ is hydrogen and A is one aromatic ring, that is unsubstituted or substituted with one methoxy group, preferably in the para-position.

When Y is an alkyloxycarbonyl group, $C_{1-30}$ alkyloxycarbonyl groups are preferred. These groups may be unsaturated, branched and/or substituted by different groups as set forth in the alcohol, aldehyde, and ketone list below. The aryloxycarbonyl group is preferably a phenyloxycarbonyl group that may be substituted as shown in the phenol list set forth below. The cycloalkyloxycarbonyl group is preferably a $C_{3-8}$ cycloalkyloxycarbonyl group which may be unsaturated and/or substituted.

When Y is an alkylcarbonyl group, $C_{1-30}$ alkyl groups are preferred. These alkyl groups may be branched, unsaturated and/or substituted, e.g. by naphthol, phenoxy, naphthyloxy, hydroxy, amino, pyrocatechol, and the groups O—CO—$OR^2$ or O—CO—$R^2$, as set forth above. When Y is a cycloalkylcarbonyl group, $C_{3-8}$ cycloalkyl moieties are preferred which may be unsaturated and/or substituted. When Y is an arylcarbonyl group, phenylcarbonyl groups are preferred which may be substituted.

When Y is an amide (N-substituted aminocarbonyl) group, a wide variety of non-organoleptic amines may be obtained upon cleavage. For example, when Y is an amide, a list of suitable primary and secondary cosmetic amines generated by this cleavage are found in the Cosmetic Ingredient Handbook edited by Joanne M. Nikitakis, which is hereby incorporated by reference as if recited in full herein. Other suitable surfactant amines formed by cleavage of these compounds may be found, for example in Surfactants Europe, edited by Gordon L. Hollis, which is hereby incorporated by reference as if recited in full herein.

Preferred N-substituted aminocarbonyl groups are those that form, after cleavage, the organoleptic amines set forth in the list below.

In formula I, it is preferred that n is 1 or 2.

In the present invention, all groups represented by Y may be substituted with one or more substituents selected from aryl, cycloalkyl, cycloalkenyl, oxo, oxy, cyano, hydroxy, a hydroxy group esterified with a carboxylic acid, a carbonic acid ester, a N,N-substituted carbamic acid or an oximino carbonic acid; amino substituted with oximinocarbonyl; an esterified carboxylic group; and a carboxylic group esterified with an oxime.

The groups represented by Y may also be substituted with the following substituents: A—CO—$CHR^1$—O—, A—CO—$CHR^1$—O—CO—, A—CO—$CHR^1$—O-alkoxy or A—CO—$CHR^1$—O—CO-alkoxy. Formula III set forth below is one example of this kind of compound, in which Y is an alkyl group substituted with A—CO—$CHR^1$—O—:

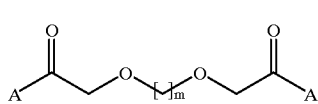

III wherein m is an integer and $R^1$ and A are defined above.

Compounds of formula I may generate the following organoleptic aryl ketones:

4-methoxyphenyl-ethanone*

1-[6-(1,1-dimethylethyl)-2,3-dihydro-1,1-dimethyl-1H-inden-4-yl]-ethanone 1-(5,6,7,8-tetrahydro-3,5,5,6,8,8-hexamethyl-2-naphthalenyl)-ethanone*

2-(1-methylethyl)-indanone*

4-tert-butyl-3,5-dinitro-2,6-dimethyl-acetophenone 1,6,7,8-tetrahydro-1,4,6,6,8,8-hexamethyl-as-indacen-3(2H)-one*

1-(2-napthalenyl)-ethanone*

1-(2,3-dihydro-1,1,2,3,3,6-hexamethyl-1H-inden-5-yl)-ethanone

1-[2,3-dihydro-1,1,2,6-tetramethyl-3-(1-methylethyl)-1H-inden-5-yl]-ethanone 3-methyl-1-(4-methylphenyl)-4-hexen-1-one 5-acetyl-1,1,2,3,3-pentamethylindane 1-phenylpropanone acetophenone*

2,4-dimethylphenyl-ethanone*

1-[4-(1,1-dimethylethyl)-2,6-dimethylphenyl]-ethanone 1-(hexahydrodimethyl-1H-benzindenyl)-ethanone*

1-(5,6,7,8-tetrahydro-2-naphthalenyl)-ethanone 1-phenyl-4-penten-1-one 1-(5,6,7,8-tetrahydro-3,5,5,8,8-pentamethyl-2-naphthalenyl)-ethanone 1-(3-ethyl-5,6,7,8-tetrahydro-5,5,8,8-tetramethyl-2-naphthalenyl)-ethanone wherein the asterisk (*) indicates preferred aryl ketones.

Compounds of formula I may generate the following ketones:

2,5-dimethyl-oct-2-en-6-one**

4-(2,6,6-trimethylcyclohex-1-en-1-yl)butan-2-one**

4-(2,6,6-trimethylcyclohex-2-en-1-yl)butan-2-one**

2-methyl-5-(1-methylethenyl)-cyclohex-2-en-1-one*

1-(4-hydroxyphenyl)-butan-3-one**

4-benzo-1,3-dioxo-5-yl-but-2-one**

2-heptyl-cyclopentanone nonan-2-one* octan-2-one*

2,2,6,10-tetrametyltricyclo-[5.4.0.0(6,10)]-undecan-4-one heptan-2-one* undecan-2-one* benzylacetone* butan-2-one*

1,2,3,5,6,7-hexahydro-1,1,2,3,3,-pentamethyl-4H-inden-4-one*

6-methyl-hept-5-en-2-one*

2-(butan-2-yl)-cyclohexanone*
2-hexyl-cyclopent-2-en-1-one*
2-(1-methylethyl)-5-methyl-cyclohexanone*
2-(2-methylethyl)-5-methyl-cyclohexanone*
3-methyl-cyclopentadecanone
4-dimethylpropyl)-cyclohexanone*
6,10-dimethyl-undeca-5,9-dien-2-one*
3-oxo-2-pentyl-cyclopentane-acetic acid methyl ester**
1-(1,2,3,4,5,6,7,8-octahydro-2,3,8,8-tetramethyl-2-naphthalenyl)-ethanone*
3-methyl-5-propyl-cyclohex-2-en-1h-one*
1-(2-cyclohexen)-2,4,4-trimethyl-but-2-enone*
carvone**
2-hexyl-cyclo-pent-2-en-1-one*
2-pentyl-cyclopent-2-en-1-one
3-methyl-2-pentyl-cyclopent-2-en-1-one*
2-hexylidene-cyclopentanone*
3,5-diethyl-5,6-dimethyl-2-cyclohexenone*
4,4a,5,6,7,8-hexahydro-6-isopropenyl-4,4a-dimethyl-2(3H)-napthalenone**
3-methyl-6-propylidenecyclohexanone*
4-(1-methylethyl)-cyclohex-2-en-1-one
(E)-oct-3-en-2-one
1-(2,3,4,7,8,8A-hexahydro-3,6,8,8-tetramethyl-1H-3A,7-methanoazulen-5-yl)-ethanone*
2-hydroxy-3,5-dimethyl-cyclopent-2-ene-1-one*
1-(3,3-dimethyl-1-cyclohexen-1-yl)ethanone*
1-(2,4,6-trimethylcyclohex-3-en-1-yl)-but-1-en-3-one
acetylisolongifolene
2-(3-methylbut-2-en-1-yl)-3-methyl-cyclopent-2-en-1-one
3-methyl-5-(2,2,3-trimethylcyclopent-3-en-1-yl)pent-3-en-2-one*
5-butylidene-2,2,4-trimethylcyclopentanone
1,2,3,5,6,7-hexahydro-1,1,2,3,3-pentamethyl-4H-inden-4-one**
3-methyl-5-propyl-cyclohex-2-en-1-one**
4,4a,5,6,7,8-hexahydro-6-isopropyl-2(3H)-naphthalenone
3,5,5-trimethyl-cyclohex-2-en-1,4-dione*
(E)-5-methyl-2-hepten-4-one
acetyl diisoamylene**
dec-3-en-2-one
2-ethyl-3,6,6-trimethylcyclohex-2-enyl-but-2-en-1-one
1-(5,5-dimethyl-1 (6)-cyclohexen-1-yl)-4-penten-1-one**
1-(2,6,6-trimethyl-1-cyclohexen-1-yl)-but-2-en-1-one**
1-(2,6,6-trimethyl-2-cyclohexen-1-yl)-but-2-en-1-one**
1-(2,6,6,trimethyl-3-cyclohexen-1-yl)-but-2-en-1-one**
2,4,4,5,5-pentamethyl-1-cyclopentene-1-yl-ethanone*
wherein one asterisk (*) indicates preferred ketones and two asterisks (**) indicate more preferred ketones.

Compounds of formula I may generate the following aldehydes:
2,6,10-trimethylundec-9-enal*
1,2,3,4,5,6,7,8-octahydro-8,8-dimethyl-2-napthalenecarboxaldehyde
tridecanal
2-[4-(1-methylethyl)phenyl]-ethanal
2,4-dimethyl-cyclohex-3-ene-1-carboxaldehyde*
4-carboxaldehyde-1,3,5-trimethyl-cyclohex-1-ene*
1-carboxaldehyde-2,4-dimethyl-cyclohex-3-ene*
1-carboxaldehyde-4-(4-hydroxy-4-methylpentyl)-cyclohex-3-ene*
hex-2-enal*
3,5,5-trimethyl-hexanal
heptanal*
2,6-dimethyl-hept-5-eneal*
decanal**
dec-9-enal
dec-4-en-1-al
2-methyldecanal*
undec-10-ene-1-al**
undecanal*
dodecanal**
2-methyl-undecanal**
tridecanal
2-tridecenal
octanal**
nonanal*
3,5,5-trimethylhexanal
2-nonenal
undec-9-enal**
2-phenyl-propanal*
4-methyl-phenyl acetaldehyde*
3,7-dimethyl-octanal*
dihydrofarnesal**
7-hydroxy-3,7-dimethyl-octanal*
2,6-dimethyl-oct-5-ene-1-al
2-(4-(1-methylethyl)phenyl)-ethanal*
3-(3-isopropyl-phenyl)-butanal**
2-(3,7-dimethyl-oct-6-en-oxy)-ethanal
1-carboxaldehyde-4-(4-methyl-3-penten-1-yl)-cyclohex-3-ene*
2,3,5,5,-tetramethyl-hexanal
longifolic aldehyde
2-methyl-4-(2,6,6-trimethylcyclohex-2-en-1-yl)-butanal*
2-methyl-3-(4-tert-butylphenyl)propanal**
4-(1,1-dimethyl-ethyl)-benzenepropanal*
2-[4-(1-methyl-ethyl)phenyl]-propanal
alpha-methyl-1,3-benzodioxole-5-propanal*
3,7-dimethyl-oct-6-en-1-al*
2-methyl-3-(p-isopropylphenyl)-propionaldehyde*
4-(4-hydroxy-4-methyl-pentyl)-cyclohex-3-en-1-carboxaldehyde**
alpha-methyl-1,3-benzodioxole-5-propanal*
1-carboxaldehyde-4-(1,1-dimethylethyl)-cyclohexane
4-(octahydro-4,7-methano-5H-inden-5-ylidene)-butanal
[(3,7-dimethyl-6-octenyl)oxy]-acetaldehyde**
3,7-dimethyl-oct-2,6-dien-1-al*
nonadienal*
2,4-dimethyl-2,6-heptadienal
trans-dec-2-en-1-al*
2,4-diethyl-hep-2,6-dien-1-al* dodec-2-en-1-al*
3,7-dimethyl-oct-2,6-dien-1-al*
2,4-diethyl-hepta-2,6-dienal
3,7-dimethyl-nona-2,6-dien-1-al*
3-propyl-2-hepten-1-al
1-carboxaldehyde-4-(prop-2-en-2-yl)-cyclohex-1-ene wherein one asterisk (*) indicates preferred aldehydes and two asterisks (**) indicate more preferred aldehydes.

Compounds of formula I may generate the following alcohols and phenols:

amyl alcohol
hexyl alcohol*
2-hexyl alcohol*
heptyl alcohol*
octyl alcohol*
nonyl alcohol*
decyl alcohol*
undecyl alcohol*
lauryl alcohol*
myristic alcohol
3-methyl-but-2-en-1-ol*
3-methyl-1-pentanol
cis-3-hexenol*
cis-4-hexenol*
3,5,5-trimethyl-hexanol
3,4,5,6,6-pentamethylheptan-2-ol*
citronellol*
geraniol*
oct-1-en-3-ol
2,5,7-trimethyl-octan-3-ol
2-cis-3,7-dimethyl-2,6-octadien-1-ol
6-ethyl-3-methyl-5-octen-1-ol*
3,7-dimethyl-oct-3,6-dienol*
3,7-dimethyloctanol*
7-methoxy-3,7-dimethyl-octan-2-ol*
cis-6-nonenol*
5-ethyl-2-nonanol
6,8-dimethyl-2-nonanol*
2,2,8-trimethyl-7(8)-nonene-3-ol
nona-2,6-dien-1-ol
4-methyl-3-decen-5-ol*
dec-9-en-1-ol
benzylalcohol
2-methyl-undecanol
10-undecen-1-ol
1-phenyl-ethanol*
2-phenyl-ethanol*
2-methyl-3-phenyl-3-propenol
2-phenyl-propanol*
3-phenyl-propanol*
4-phenyl-2-butanol
2-methyl-5-phenyl pentanol*
2-methyl-4-phenyl-pentanol*
3-methyl-5-phenyl-pentanol*
2-(2-methylphenyl)-ethanol*
4-(1-methylethyl)-benzene methanol
4-(4-hydroxyphenyl)-butan-2-one*
2-phenoxy-ethanol*
4-(-methylethyl)-2-hydroxy-1-methyl benzene
2-methoxy-4-methyl-phenol
4-methyl-phenol
anisic alcohol*
p-tolyl alcohol*
cinnamic alcohol*
vanillin*
ethyl vanillin*
eugenol*
isoeugenol*
thymol
anethol*
decahydro 2-naphthalenol
bomeol*
cedrenol*
famesol*
fenchyl alcohol*
menthol*
3,7,11-trimethyl-2,6,10-dodecatrien-1-ol
alpha ionol*
tetrahydro ionol*
2-(1,1-dimethylethyl)-cyclohexanol*
3-(1,1-dimethylethyl)-cyclohexanol*
4-(1,1-dimethylethyl)-cyclohexanol*
4-isopropyl cyclohexanol
6,6-dimethyl-bicyclo[3.3.1]hept-2-ene-2-ethanol
6,6-dimethyl-bicyclo[3.1.1]hept-2-ene-methanol*
p-menth-8-en-3-ol*
3,3,5-trimethyl-cyclohexanol
2,4,6-trimethyl-3-cyclohexenyl-methanol*
4-(1-methylethyl)-cyclohexane-methanol*
4-(1,1-dimethylethyl)-cyclohexanol
2-(1,1-dimethylethyl)-cyclohexanol
2,2,6-trimethyl-alpha-propyl cyclohexane propanol*
5-(2,2,3-trimethyl-3-cyclo-pentenyl)-3-methylpentan-2-ol*
3-methyl-5-(2,2,3-trimethylcyclopentyl-3-enyl)-pent-4-en-2-ol*
2-ethyl-4(2,2,3-trimethylcyclopentyl-3-enyl)-but-2-en-1-ol*
4-(5,5,6-trimethylbicyclo[2.2.1]hept-2-yl)-cyclohexanol*
2-(2-methylpropyl)-4-hydroxy-4-methyl-tetrahydropyran*
2-cyclohexyl propanol*
2-(1,1-dimethylethyl)-4-methyl-cyclohexanol*
1-(2-tert-butyl-cyclohexyloxy)-2-butanol*
1-(4-isopropyl-cyclohexyl)-ethanol*
1-(4-hydroxyphenyl)-butan-3-one
2,6-dimethyl-oct-7-en-2-ol*
2,6-dimethyl-heptan-2-ol*
3,7-dimethyl-octa-1,6-dien-3-ol* wherein one asterisk (*) indicates preferred alcohols and phenols.

Compounds of formula I may generate the following organoleptic amines:

anthranilic acid 1-methyl-1-(4-methyl-3-cyclohexen-1-yl)ethyl ester benzopyrrole
8,8-di(1H-indol-1-yl)-2,6-dimethyl-octane-2-ol
anthranilic acid allyl ester
anthranilic acid 1,5-dimethyl-1-vinyl-4-hexenyl ester
2-amino-benzoic acid methyl ester*
methyl anthranilic acid N-(2-methylpent-1-en-1-yl) ester
1-methyl-1-(4-methyl-3-cyclohexen-1-yl)ethyl anthranilic acid
anthranilic acid phenylethyl ester*
2-methylamino-benzoic acid methyl ester*
6-methyltetrahydro-quinoline
isobutyl N-methyl anthranilate
(Z)-3-hexenyl-2-aminobenzoate*
wherein one asterisk (*) indicates preferred organoleptic amines.

Compounds of formula I may generate the following organoleptic nitriles:
dodecanenitrile*
tetradecanenitrile*
5-methyl-7-(1-methylethyl)-bicyclo[2.2.2]oct-5-ene-2-carbonitrile*
1,2,3,4-tetrahydro-4,4-dimethyl-1-naphthalenecarbonitrile*
2,4-dimethyl-cyclohex-3-ene-1-nitrile
2,2,3-trimethyl-3-cyclopentene-1-acetonitrile
4-(1,1-dimethylethyl)-benzeneacetonitrile
3,12-tridecadienenitrile
3-methyl-octanenitrile
3-methyl-dodecanenitrile
2-methyl-decanenitrile
decanenitrile
octanenitrile
4,6,6-trimethyl-heptanenitrile
isotetradecanenitrile
3,3-dimethyl-bicyclo[2.2.1]heptane-2-carbonitrile
octahydro-4,7-methano-indene-5-carbonitrile
3,7,7-trimethyl-4-propylidenenitrile-bicyclo[4.1.0]heptane
3-hexyloxy-propionitrile
3-(3,7-dimethyl-oct-2,6-dienyloxy)-propionitrile*
5-cyano-pentan-2-one*
3-methyl-5-cyano-pentan-2-one
4-cyano-2,2-dimethyl-butanal
2-(2-cyanoethyl)-cyclohexanone
3,7-dimethyl-octa-2,6-diennitrile*
3-methyl-5-phenyl-pent-2-enenitrile
3,7-dimethyl-oct-6-enenitrile*
1,2,3,4,5,6,7,8-octahydro-8,8-dimethyl-2-napthalenecarbonitrile
3-methyl-2(3)-nonenenitrile
2-propyl-2-hexenenitrile
4-methyl-2-propyl-hex-2-enenitrile
tridec-2-enenitrile
3,7-dimethyl-nona-2,6-diennitrile*
2,3-dimethyl-2-nonenenitrile
2-undecenenitrile*
cyclohexylidene-phenyl-acetonitrile*
wherein one asterisk (*) indicates preferred nitriles.

Compounds of formula I may generate the following preferred organoleptic oximes:
1,5-dimethyl-bicyclo[3.2.1]octan-8-one oxime
2,4,4,7-tetramethylnona-6,8-dien-3-one oxime
5-methyl-heptan-3-one oxime
1-bicyclo[2.2.1]hept-5-en-2-yl-ethanone oxime Obviously, it is not possible to provide a complete list of the organoleptic and/or antimicrobial aryl and heteroaryl ketones, ketones, aldehydes, alcohols, phenols, amines, nitriles, thiols, oximes, and lactones that are generated as a result of the desired cleavage of the ketones of formula I. All such compounds, however, are considered to be within the scope of the present invention. One skilled in the art will be able to identify such compounds based on the present specification which provides sufficient disclosure to obtain the desired organoleptic, e.g. fragrance and odor masking and/or antimicrobial effects.

Preferably, the compounds of formula I may be used as sustained release odorants. These compounds may also be used as sustained agents to mask or attenuate undesirable odors or to provide additional odors initially present in consumer products. As used herein, the phrase "consumer products" is intended to include, for example, laundry detergents, fabric softeners, fabric softener sheets, cleaning compositions, swimming pool additives, toiletries, and cosmetic products, such as shampoo, conditioners and sunscreens. Further applications for the present compounds are sustained-release antimicrobial agents in the same products.

The amount of a compound of formula I required to produce a desired, overall effect varies depending upon the particular compound selected, the product in which it will be used, and the particular effect desired.

For example, depending upon the identity and concentration of the compound selected, when a compound of formula I is added either singly or as a mixture to, for example, a laundry product at levels ranging from about 0.001 to about 10% by weight, an odorant, i.e. an odoriferous aryl ketone, ketone, aldehyde, alcohol, phenol, amine, lactone, thiol, oxime, nitrile or two or three of these odoriferous substances in an organoleptically effective amount is/are released when the product is used. These newly formed odorant(s) serve to enhance the odor of the fragrance. Depending on the compound of formula I, an antimicrobial agent may be released.

As is evident from the compilation of organoleptic substances set forth above, a broad range of known odorants may be generated from the precursor compounds of the present invention. While manufacturing compositions, the precursors of the present invention may be used according to methods known to the perfumer, such as e.g. from W. A. Poucher, Perfumes, Cosmetics, Soaps, 2, 7th Edition, Chapman and Hall, London 1974, which is hereby incorporated by reference as if recited in full herein.

The compounds of formula I may be prepared using standard methods known to the skilled chemist.

The following examples are provided to further illustrate methods of preparation of the compounds of the present invention, as well as certain physical properties and uses thereof. These examples are illustrative only and are not intended to limit the scope of the invention in any way.

EXAMPLE 1

Synthesis of p-Methoxyphenacyl acetate

To a solution of 63 g potassium acetate in 750 ml of methanol, 92.9 g of 4-methoxyphenacyl bromide was dropped in. The resulting solution was refluxed for 4 hours, then cooled and poured into water. The aqueous layer was extracted with ether, then the combined organic phases were washed with water, dried, and evaporated to dryness. The resulting solid was recrystallized from methanol to yield 54.5 g crystals.

NMR (CDCl$_3$)δ 8.05–7.70 (m, 2H), 7.10–6.70 (m, 2H), 5.30 (s, H), 3.90 (s, 3H), 2.20 (s, 3H)ppm.

EXAMPLE 2

Synthesis of p-Tolyloxy-acetic acid 2-oxo-2-phenyl-ethyl ester

According to the procedure of Example 1, p-tolyloxy-acetic acid 2-oxo-2-phenyl-ethyl ester was prepared from (4-methylphenoxy) acetic acid and 2-bromoacetophenone.

EXAMPLE 3

Synthesis of 2-Amino-3-(3,4-dihydroxy-phenyl)-propionic acid 2-oxo-2-phenyl-ethyl ester According to the procedure of Example 1, 2-amino-3-(3,4-dihydroxy-phenyl)-propionic acid 2-oxo-2-phenyl-ethyl ester was prepared from 3-(3,4-dihydroxy phenyl)alanine and 2-bromoacetophenone.

EXAMPLE 4

Synthesis of Acetic acid 1-methyl-2-oxo-2-phenyl-ethyl ester

According to the procedure of Example 1, acetic acid 1-methyl-2-oxo-2-phenyl-ethyl ester was prepared from acetic acid and 2-bromo-1-phenyl-1-propan-1-one.

EXAMPLE 5

Synthesis of (Naphthalen-2-yloxy)-acetic acid 2-(4-methoxy-phenyl)-2-oxo-ethyl ester According to the procedure of Example 1, (naphthalen-2-yloxy)-acetic acid 2-(4-methoxy-phenyl)-2-oxo-ethyl ester was prepared from (2-naphthoxy)acetic acid and 4-methoxy-phenacyl bromide.

EXAMPLE 6

Synthesis of Cyclopropane carboxylic acid 2-naphthalen-2-yl-2-oxo-ethyl ester

According to the procedure of Example 1, cyclopropane carboxylic acid 2-naphthalen-2-yl-2-oxo-ethyl ester was prepared from cyclopropane carboxylic acid and 2-bromo-1-naphthalen-2-yl-ethanone.

EXAMPLE 7

Synthesis of Acetic acid 2-(3-ethyl-5,5,8,8-tetramethyl-5,6,7,8-tetrahydro-naphthalen-2-yl)-2-oxo-ethyl ester According to the procedure of Example 1, acetic acid 2-(3-ethyl-5,5,8,8-tetramethyl-5,6,7,8-tetrahydro-naphthalen-2-yl)-2-oxo-ethyl ester was prepared from acetic acid and 2-bromo-1-(3-ethyl-5,5,8,8-tetramethyl-5,6,7,8-tetrahydro-naphthalen-2-yl)-ethanone.

EXAMPLE 8

Synthesis of 3-(3-Isopropylphenyl)butanol

To a refluxing solution of 132.8 g aluminum isopropoxide in 800 ml of isopropanol, a solution of 300 g of 3-(3-isopropylphenyl)butanal in 200 ml of isopropanol was dropped in. The resulting solution was refluxed for 1.5 hours, then cooled and diluted with ether. Then, the organic phase was washed with brine, dried, and evaporated to dryness. The resulting oil was distilled to yield 223.5 g of a colorless oil.

NMR (CDCl$_3$)δ 7.30–6.96 (m, 4H), 3.69–3.43 (t, 2H), 2.99–2.73 (m, 2H), 1.92–1.77 (m, 2H), 1.60–1.44 (br s, OH), 1.39–1.19 (m, 9H)ppm.

EXAMPLE 9

Synthesis of Octyloxy-acetonitrile

To a suspension of 15.60 g sodium hydride (60%) in 200 ml of 1,2-dimethoxyethane, 50.79 g of 1-octanol was dropped in. The mixture was stirred for 45 minutes at room temperature. Then, 46.76 g of bromoacetonitrile was dropped in. The reaction mixture was refluxed for 2 hours, quenched with water, filtered, and diluted with brine. After extraction with ether, the organic layer was washed with brine and water, dried, filtered, and evaporated to dryness. The resulting dark oil was purified by distillation to yield a yellow oil.

NMR (CDCl$_3$)δ 4.24 (s, 2H), 3.63–3.52 (t, 2H), 1.75–1.50 (m, 2H), 1.49–1.15 (m, 1OH), 0.96–0.80 (t, 3H)ppm.

EXAMPLE 10

Synthesis of Undec-10-enyloxy-acetonitrile

According to the procedure of Example 9, undec-10-enyloxy-acetonitrile was prepared from undec-10-en-1-ol, bromoacetonitrile, and sodium hydride.

EXAMPLE 11

Synthesis of [3-(3-Isopropyl-phenyl)-butoxy]-acetonitrile

According to the procedure of Example 9, [3-(3-isopropyl-phenyl)-butoxy]-acetonitrile was prepared from 3-(3-isopropylphenyl)butanol, bromoacetonitrile, and sodium hydride.

EXAMPLE 12

Synthesis of [1-Methyl-3-(2,6,6-trimethyl-cyclohex-1-enyl)-allyloxy]-acetonitrile According to the procedure of Example 9, [1-methyl-3-(2,6,6-trimethyl-cyclohex-1-enyl)-allyloxy]-acetonitrile was prepared from 4-(2,6,6-trimethyl-cyclohex-1-enyl)but-3-en-2-ol (Marvell et al., J. Org. Chem., 37 (1972) 19, 2992–97), bromoacetonitrile, and sodium hydride.

EXAMPLE 13

Synthesis of (2-Pentyl-3-phenyl-allyloxy)-acetonitrile

According to the procedure of Example 9, (2-pentyl-3-phenyl-allyloxy)-acetonitrile was prepared from amyl cinnamic alcohol, bromoacetonitrile, and sodium hydride.

EXAMPLE 14

Synthesis of 2-(3,7-Dimethyl-oct-6-enyloxy)-1-naphthalen-2-yl-ethanone

To a suspension of 2.24 g of magnesium in ether, a solution of 19.09 g 2-bromonaphthalene in 80 ml of ether was dropped. The mixture was heated to reflux. After refluxing for one hour, the mixture was cooled to 0–5° C. and a solution of 15.00 g (3,7-dimethyl-oct-6-enyloxy)-acetonitrile (Kulka, K. et al., Perfumer & Flavorist Vol. 3 (1978), p.39) in 20 ml of ether was dropped in at this temperature. After stirring at room temperature for 3 hours, the mixture was quenched with water and aqueous sulfuric acid. After extracting with ether, the combined organic phases were washed with saturated sodium bicarbonate and water, dried, filtered, and evaporated to dryness. The resulting dark oil was purified by chromatography to yield 15.22 g of a yellow oil.

NMR (CDCl$_3$)δ 8.49 (s, 1H), 8.05–7.79 (m, 4H), 7.67–7.42 (m, 2H), 5.15–5.01 (t, 1H), 4.83 (s, 2H), 3.73–3.55 (t, 2H), 2.11–1.83, (m, 2H), 1.82–1.03 (m, 11H), 0.96–0.81 (d, 3H)ppm.

EXAMPLE 15

Synthesis of 2-Ethoxy-1-phenyl-ethanone

According to the procedure of Example 12, 2-ethoxy-1-phenylethanone was prepared from bromobenzene and ethoxyacetonitrile.

EXAMPLE 16

Synthesis of 1-Naphthalen-2-yl-2-octyloxy-ethanone

According to the procedure of Example 12, 1-naphthalen-2-yl-2-octyloxy-ethanone was prepared from 2-bromonaphthalene and octyloxy-acetonitrile.

EXAMPLE 17

Synthesis of 2-(3,7-Dimethyl-oct-6-enyloxy)-1-(4-methoxy-phenyl)-ethanone

According to the procedure of Example 12, 2-(3,7-Dimethyl-oct-6-enyloxy)-1-(4-methoxy-phenyl)-ethanone was prepared from 4-bromoanisole and (3,7-dimethyl-oct-6-enyloxy)-acetonitrile (Kulka, K. et al., Perfumer & Flavorist Vol. 3 (1978), p.39).

EXAMPLE 18

Synthesis of 2-(3,7-Dimethyl-oct-6-enyloxy)-1-(4-hydroxy-phenyl)-ethanone

According to the procedure of Example 12, 2-(3,7-Dimethyl-oct-6-enyloxy)-1-(4-hydroxy-phenyl)-ethanone was prepared from (4-bromo-phenoxy)-trimethyl-silane (J. Org. Chem., 48 (1983), 1543) and (3,7-dimethyl-oct-6-enyloxy)-acetonitrile (Kulka, K. et al., Perfumer & Flavorist Vol. 3 (1978), p.39).

EXAMPLE 19

Synthesis of 1-Naphthalen-2-yl-2-undec-10-enyloxy-ethanone

According to the procedure of Example 12, 1-naphthalen-2-yl-2-undec-10-enyloxy-ethanone was prepared from 2-bromonaphthalene and undec-10-enyloxy-acetonitrile.

EXAMPLE 20

Synthesis of 2-[3-(3-Isopropyl-phenyl)-butoxy]-1-naphthalen-2-yl-ethanone

According to the procedure of Example 12, 2-[3-(3-isopropylphenyl)-butoxy]-1-naphthalen-2-yl-ethanone was prepared from 2-bromonaphthalene and [3-(3-isopropyl-phenyl)-butoxy]acetonitrile.

EXAMPLE 21

Synthesis of 2-[3-(3-Isopropyl-phenyl)-butoxy]-1-(4-methoxy-phenyl)-ethanone

According to the procedure of Example 12, 2-[3-(3-isopropyl-phenyl)-butoxy]-1-(4-methoxy-phenyl)-ethanone was prepared from 4-bromoanisole and [3-(3-isopropyl-phenyl)-butoxy]-acetonitrile.

EXAMPLE 22

Synthesis of 2-(3,7-Dimethyl-oct-6-enyloxy)-1-phenantren-9-yl-ethanone

According to the procedure of Example 12, 2-(3,7-dimethyl-oct-6-enyloxy)-1-phenantren-9-yl-ethanone was prepared from 9-bromo-phenantrene and (3,7-dimethyl-oct-6-enyloxy)-acetonitrile (Kulka, K. et al., Perfumer & Flavorist Vol. 3 (1978), p.39).

EXAMPLE 23

Synthesis of 1-(4-Methoxy-phenyl)-2-[1-methyl-3-(2,6,6-trimethyl-cyclohex-1-enyl)-allyloxy]-ethanone According to the procedure of Example 12, 1-(4-methoxy-phenyl)-2-[1-methyl-3-(2,6,6-trimethyl-cyclohex-1-enyl)-allyloxy]-ethanone was prepared from 4-bromoanisole and [1-methyl-3-(2,6,6-trimethyl-cyclohex-1-enyl)-allyloxy]-acetonitrile.

EXAMPLE 24

Synthesis of 1-(4-Methoxy-phenyl)-2-(2-pentyl-3-phenyl-allyloxy)-ethanone

According to the procedure of Example 12, 1-(4-methoxy-phenyl)-2-(2-pentyl-3-phenyl-allyloxy)-ethanone was prepared from 4-bromoanisole and (2-pentyl-3-phenyl-allyloxy)-acetonitrile.

EXAMPLE 25

Synthesis of Hydroxy-acetic acid 2-oxo-2-phenyl-ethyl ester

A mixture of 7.61 g of glycolic acid, 19.90 g of phenacylbromide and 13.9 ml of triethylamine in 300 ml of ethyl acetate was stirred for 20 hours at room temperature. Then, the mixture was filtered. The filtrate was washed with 2N HCl, saturated sodium bicarbonate, and brine. Then, the filtrate was dried, filtered again, and evaporated to dryness. The resulting white solid was purified by recrystallization to yield 11.85 g of colorless crystals.

NMR (CDCl$_3$)δ 7.97–7.86 (m, 2H), 7.71–7.44 (m, 3H), 5.49 (s, 2H), 4.45–4.36 (d, 2H), 2.59–2.47 (t, 1H)ppm.

EXAMPLE 26

Synthesis of Carbonic acid 4-allyl-2-methoxy-phenyl ester 2-(4-methoxy-phenyl)-2-oxo-ethyl ester To a solution of 17.62 g of 2-hydroxy-4'-methoxyacetophenone (Kovach et al., J. Amer. Chem. Soc., Vol. 115, No. 23, (1993) p. 10476) and 12.96 g of pyridine in 240 ml of dichloromethane, a solution of 26.32 g of eugenol-chloroformate in 60 ml of dichloromethane was dropped in at 5–10° C. Then, the mixture was stirred for 6 hours at room temperature. The reaction mixture was then acidified with 2N HCl and extracted with ether. The combined organic phases were washed with 2N HCl, saturated sodium bicarbonate and brine, and then dried, filtered, and evaporated to dryness. The resulting solid was purified by recrystallization to yield 29.79 g of yellow crystals.

NMR (CDCl$_3$)δ 7.98–7.86 (m, 2H), 7.20–6.72 (m, 5H), 6.09–5.83 (m, 1H), 5.41 (s, 2H), 5.18–5.02 (m, 2H), 3.89 (s, 3H), 3.87 (s, 3H), 3.43–3.32 (d, 2H)ppm.

EXAMPLE 27

Synthesis of Carbonic acid 3-methyl-5-phenyl-pentyl ester 2-naphthalen-2-yl-2-oxo-ethyl ester According to the procedure of Example 22, carbonic acid 3-methyl-5-phenyl-pentyl ester 2-naphthalen-2-yl-2-oxo-ethyl ester was prepared from 2-hydroxy-1-naphthalen-2-yl-ethanone (Langenbeck et al., Chem. Ber., 69 (1936) 514–516), 3-methyl-5-phenyl-pentanol-chloroformate, and pyridine.

EXAMPLE 28

Synthesis of 4-Hydroxy-undecanoic acid sodium salt

To a solution of 43.6 g of sodium hydroxide in 150 ml of methanol heated to reflux, 200 g of gamma-undecalactone was dropped in. After stirring for 2 hours at reflux, the mixture was cooled to room temperature and evaporated to dryness. The resulting crystals were washed with hexane to yield 240 g of colorless crystals.

NMR (CDCl$_3$)δ 5.1–4.8 (br s, OH), 3.63–3.42 (m, 1H), 2.39–2.20 (t, 2H), 1.89–1.52(m, 2H), 1.51–1.15 (m, 12H), 1.00–0.81, (t, 3H) ppm.

EXAMPLE 29

Synthesis of 4-Hydroxy-undecanoic acid-2-naphthalen-2-yl-2-oxo-ethyl ester

A suspension of 20.00 g of 2-bromo-2'-acetonaphtone, 18.01 g of 4-hydroxy-undecanoic acid sodium salt, and 0.5 g of tetrabutylammonium bromide in 180 ml of dimethylformamide was stirred for 6 hours at 50° C. Then, the reaction mixture was diluted with ether and washed with water, 2N HCl, saturated sodium bicarbonate, and brine. Then, the mixture was dried, filtered, and evaporated to dryness. The resulting solid was purified by recrystallization to yield 7.92 g of colorless crystals.

NMR (CDCl$_3$)δ 8.41 (s, 1H), 8.03–7.78 (m, 4H), 7.70–7.48 (m, 2H), 5.55–5.42 (2s, 2H), 3.80–3.61 (m, 1H), 2.27–2.60 (t, 2H), 2.33–2.06 (br s, OH), 2.05–1.11 (m, 14H), 1.02–0.79 (t, 3H)ppm.

EXAMPLE 30

Synthesis of 4-Hydroxy-undecanoic acid 2-(4-methoxy-phenyl)-2-oxo-ethyl ester

According to the procedure of Example 24, 4-hydroxy-undecanoic acid 2-(4-methoxy-phenyl)-2-oxo-ethyl ester was prepared from 2-bromo-4'-methoxyacetophenone, 4-hydroxy-undecanoic acid sodium salt, and tetrabutylammonium bromide.

EXAMPLE 31

Synthesis of 4-Hydroxy-undecanoic acid 1-methyl-2-oxo-2-phenyl-ethyl ester

According to the procedure of Example 24, 4-hydroxy-undecanoic acid 1-methyl-2-oxo-2-phenyl-ethyl ester was prepared from 2-bromopropiophenone, 4-hydroxy-undecanoic acid sodium salt, and tetrabutylammonium bromide.

EXAMPLE 32

Synthesis of 4-(3-Methyl-5-phenyl-pentyloxycarbonyloxy)-undecanoic acid 2-naphthalen-2-yl-2-oxo-ethyl ester To a solution of 4.00 g of 4-hydroxy-undecanoic acid-2-naphthalen-2-yl-2-oxo-ethyl ester and 1.71 g of pyridine in 20 ml of THF, a solution of 2.91 g of 3-methyl-5-phenyl-pentanol-chloroformate in 10 ml of THF was dropped in at 0° C. The mixture was stirred for 3 hours at room temperature. Then, the reaction mixture was quenched with water and extracted with ether. The organic phase was washed with 2N HCl, saturated sodium bicarbonate, and water. Then, the mixture was dried, filtered, and evaporated to dryness. The resulting yellow oil was purified by chromatography to yield 5.46 g of a colorless oil.

NMR (CDCl$_3$)δ 8.42 (s, 1H), 8.03–7.80 (m, 4H), 7.70–7.45 (m, 2H), 7.35–7.03(m, 5H), 5.49 (s, 2H), 4.89–4.71 (m, 1H), 4.30–4.07 (m, 2H), 2.80–2.45(m, 4H), 2.21–1.12 (m, 19H), 1.10–0.78 (m, 6H)ppm.

EXAMPLE 33

Synthesis of 4-Hex-3-enyloxycarbonyloxy-undecanoic acid 2-(4-methoxy-phenyl)-2-oxo-ethyl ester According to the procedure of Example 26, 4-hex-3-enyloxycarbonyloxy-undecanoic acid 2-(4-methoxy-phenyl)-2-oxo-ethyl ester was prepared from 4-hydroxy-undecanoic acid 2-(4-methoxy-phenyl)-2-oxo-ethyl ester, cis-hex-3-enol-chloroformate, and pyridine.

EXAMPLE 34

Synthesis of 4-(3-Methyl-5-phenyl-pentyloxycarbonyloxy)-undecanoic acid 1-methyl-2-oxo-2-phenyl-ethyl ester According to the procedure of Example 26, 4-(3-methyl-5-phenyl-pentyloxycarbonyloxy)-undecanoic acid 1-methyl-2-oxo-2-phenyl-ethyl ester was prepared from 4-hydroxy-undecanoic acid 1-methyl-2-oxo-2-phenyl-ethyl ester, 3-methyl-5-phenyl-pentanol-chloroformate, and pyridine.

EXAMPLE 35

Synthesis of 4-[2-Ethyl-4-(2,2,3-trimethyl-cyclopent-3-enyl)-but-2-enyloxycarbonyloxy]-undecanoic acid 1-methyl-2-oxo-2-phenyl-ethyl ester According to the procedure of Example 26, 4-[2-ethyl-4-(2,2,3-trimethyl-cyclopent-3-enyl)-but-2-enyloxycarbonyloxy]-undecanoic acid 1-methyl-2-oxo-2-phenyl-ethyl ester was prepared from 4-hydroxy-undecanoic acid 1-methyl-2-oxo-2-phenyl-ethyl ester, 2-ethyl-4-(2,2,3- trimethyl-cyclopentyl-3-en-1-yl)-but-2-en-1-ol, chloroformate, and pyridine.

EXAMPLE 36

Synthesis of 4-[12-Dimethyl-4-(2,2,3-trimethyl-cyclopent-3-enyl)-but-3-enyloxycarbonyloxy]-undecanoic acid 1-methyl-2-oxo-2-phenyl-ethyl ester According to the procedure of Example 26, 4-[1,2-dimethyl-4-(2,2,3-trimethyl-cyclopent-3-enyl)-but-3-enyloxycarbonyloxy]-undecanoic acid 1-methyl-2-oxo-2-phenyl-ethyl ester was prepared from 4-hydroxy-undecanoic acid 1-methyl-2-oxo-2-phenyl-ethyl ester, 3-methyl-5-(2,2,3-trimethyl-3-cyclopenten-1-yl)-4-penten-2-ol, chloroformate, and pyridine.

EXAMPLE 37

Light Activation of Formula I Compounds in Detergent

Samples of test cloth were washed with detergent to which one or more of the precursors of Examples 1–7, 12–22, and 24–26 had been added. The cloth samples were then line dried it either in sunlight or in the dark. The cloth dried in sunlight had a distinct fragrance note, as determined by a trained panel. In contrast, the cloth dried without light was olfactively neutral.

EXAMPLE 38

Light Activation of Formula I Compounds in Fabric Softener

Samples of test cloth were washed with a detergent. Then, a fabric softener containing one or more of the precursors of Examples 1–7, 12–22, and 24–26 was added to the rinse cycle. The cloth samples were then line dried either in sunlight or in the dark. The cloth dried in sunlight had a distinct fragrance note, as determined by a trained panel. In contrast, the cloth dried without sunlight was olfactively neutral.

EXAMPLE 39

Preparation of an O/W sunscreen lotion UV-B and UV-A

A sunscreen lotion containing 0.5% of one or more compounds of Examples 1–7, 12–22, and 24–26 was prepared as set forth below:

| RECIPE % | COMPOUND |
|---|---|
| PART A: | |
| 2% | Octyl methoxycinnamate |
| 3% | 4-4-Butyl-4'methoxydibenzoyl methane |
| 12% | Coco-caprylate/caprate |
| 4% | Isostearyl neopentanoate |
| 0.25% | Diethyleneglycol monostearate |
| 1% | Cetylalcohol |
| 0.25% | Methyl-propylparaben |
| 0.1% | EDTA-sodium salt |
| 1% | Diethanolamine cetylphosphate |

| RECIPE % | COMPOUND |
|---|---|
| PART B: | |
| 20% | Acrylate C10–C30 Alkylacrylate |
| 50.1% | water deionized |
| 5% | 1,2-Propanediol |
| 0.8% | Potassium hydroxide |

Part A was heated in a reactor to 85° C.

Part B was slowly added to Part A within 10 minutes, followed by addition of KOH and 0.5% of one or more of the compounds in Examples 1–7, 12–22, and 24–26. The emulsion was then cooled and degassed.

EXAMPLE 40 a) A fabric softener of the ester quat type (4× concentrate) is made as follows:

| INGREDIENT | CHEMICAL NAME | % |
|---|---|---|
| PART A: | | |
| Deonized Water | | to100.0 |
| MgCl$_2$ (saturated sol.) | Magnesium chloride | 1.0 |
| PART B: | | |
| REWOQUAT WE 18 | Di-(tallow-carboxyethyl) hydroxy ethyl methylammonium methosulfate | 15.0 |
| GENAPOL O 100 | Ethoxylated fatty alcohol C16–C18 10EO | 2.0 |
| ANTIFOAM DB 31 | | 0.5 |
| PART C: | | |
| Isopropyl Alcohol | | 3.0 |
| Preservative | | Qs |
| Perfume | | Qs |

While stirring and heating to 65° C., part A was mixed. Part B was then preheated to 65° C and added to part A. After cooling to room temperature, part C was added to the mixture of parts A and B. The pH value of the finished product was 2.60. The recommended level of perfume was 1.0%. The delayed release fragrances of Examples 1–7, 12–22, and 24–26 may be any part of this 1.0%.

b) Fabric softener of the ester quat type (1× concentrate):

| INGREDIENT | CHEMICAL NAME | % |
|---|---|---|
| PART A: | | |
| DEIONIZED WATER | | to100.0 |
| PART B: | | |
| REWOQUAT WB 18 | Di-(tallow-carboxyethyl)hydroxy ethyl methylammonium methosulfate | 6.0 |
| DOBANOL 25-9 | Ethoxylated fatty alcohol C12–C15 9EO | 0.50 |
| ANTIFOAM DB 31 | | 0.10 |
| PART C: | | |
| MYACIDE BT 30 | 2-bromo-2-nitropropane 1,3 diol | 0.03 |
| PROXEL GXL | Benzisothiazolinone sodium salt | 0.02 |
| Perfume | | Qs |

While stirring and heating to 65° C., part A was mixed. Part B was then preheated to 65° C. and added to part A. After cooling to room temperature, part C was added to the mixture of parts A and B. The pH value of the finished product was 3.50. The recommended level of perfume was 0.3%. The delayed release fragrances of Examples 1–7, 12–22, and 24–26 may be any part of this 0.3%.

The invention being thus described, it will be obvious that the same may be varied in many ways. Such variations are not to be regarded as a departure from the spirit and scope of the invention and all such modifications are intended to be included within the scope of the following claims.

We claim:

1. A ketone of formula I

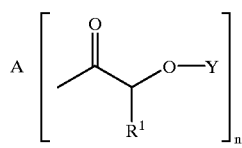

wherein

Y is an optionally substituted alkyl, cycloalkyl, or cycloalkylalkyl, wherein each alkyl group is straight or branched and each alkyl and cycloalkyl group is saturated or unsaturated;

$R^1$ is hydrogen or a $C_{1-6}$ alkyl group which is substituted, saturated or unsaturated, straight or branched;

A is a chromophoric aromatic ring or ring system, and carries 1 to 8 substituents selected from the group consisting of hydrogen, hydroxy, mercapto, amino, acyl, ester, esterified hydroxy group, cyano, nitro, substituted, saturated or unsaturated, straight or branched alkyl, alkoxy, alkylthio, and arylalkoxy groups, substituted or unsubstituted aryl groups, and a polymeric group;

n is 1 or 2; and with the proviso that formula I is not 2-ethoxy-1-phenyl-ethanone.

2. A ketone according to claim 1 wherein one or more organoleptic compounds are formed therefrom after cleavage by an activation signal.

3. A ketone according to claim 2 wherein the activation signal is selected from the group consisting of light, heat, hydrolysis, and enzymes.

4. A ketone according to claim 3 wherein two or more organoleptic compounds are formed therefrom after cleavage.

5. A ketone according to claim 1 wherein an organoleptic aryl ketone of formula II is formed after cleavage:

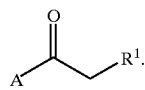

6. A ketone according to claim 1 wherein one or more organoleptic aldehyde or ketone derived from O—Y is formed after cleavage of the ketone.

7. A ketone according to claim 1 wherein an organoleptic alcohol, phenol, aldehyde, or ketone derived from Y is formed after cleavage of the ketone.

8. A ketone according to claim 1 wherein an organoleptic lactone derived from Y is formed after cleavage of the ketone.

9. A ketone according to claim 1 wherein an organoleptic amine derived from Y is formed after cleavage of the ketone.

10. A ketone according to claim 1 wherein $R^1$ is hydrogen or methyl.

11. A ketone according to claim 1 wherein $R^1$ is hydrogen or methyl and A carries no more than three substituents.

12. A ketone according to claim 11 wherein the substituents of A are methyl groups.

13. A ketone according to claim 1 wherein $R^1$ is hydrogen and A is an aromatic ring that is substituted with one methoxy group.

14. A ketone according to claim 13 wherein the methoxy group is in the para position.

15. A ketone according to claim 1 wherein A is a ring system of the formula:

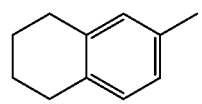

or

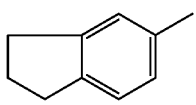

and both rings may be substituted.

16. A ketone according to claim 15 wherein one or both rings are substituted with one or more methyl groups.

17. A ketone according to claim 1 wherein a substituent of A is a polymeric group.

18. A ketone according to claim 1 wherein Y is substituted with one or more substituents selected from the group consisting of aryl, cycloalkyl, cycloalkenyl, oxo, oxy, cyano, amino, hydroxy, a hydroxy esterified carboxylic acid, a carbonic acid ester (carbonate), an N,N-substituted carbamic acid (carbamate), an oximino carbonic acid, an amino substituted oximinocarbonyl, an esterified carboxylic group, and a carboxylic esterified oxime.

19. A precursor of an active compound comprising a ketone of the formula I:

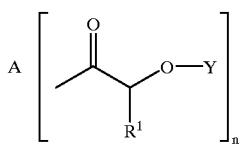

wherein

Y is an optionally substituted alkyl, cycloalkyl, cycloalkylalkyl, alkylcarbonyl, cycloalkylcarbonyl, arylcarbonyl, alkyloxycarbonyl, cycloalkyloxycarbonyl, aryloxycarbonyl, amide, oximinocarbonyl, alkylthiocarbonyl, cycloalkylthiocarbonyl, wherein each alkyl group may be straight or branched and each alkyl and cycloalkyl group may be saturated or unsaturated;

$R^1$ is hydrogen or a $C_{1-6}$ alkyl group that may be substituted, saturated or unsaturated, straight or branched;

A is a chromophoric aromatic ring or ring system, and A carries 1 to 8 substituents selected from the group consisting of hydrogen, hydroxy, mercapto, amino, acyl, ester, esterified hydroxy group, cyano, nitro;

substituted, saturated or unsaturated, straight or branched alkyl, alkoxy, alkylthio and arylalkoxy groups, substituted or unsubstituted aryl groups, and a polymeric group; and n is 1 or 2.

20. A precursor according to claim 19 wherein the active compound is a fragrance and/or an antimicrobial agent.

21. A composition selected from the group consisting of detergents, fabric softeners, personal care products, cleaning compositions, cosmetics, and sun protection products in admixture with the precursor of claim 20.

22. A method of imparting a sustained release odorant and/or an antimicrobial agent into a consumer product comprising mixing the consumer product with at least one compound according to formula I:

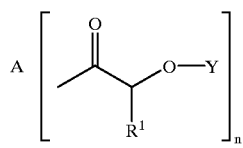

wherein

Y is an optionally substituted alkyl, cycloalkyl, or cycloalkylalkyl, wherein each alkyl group is straight or branched and each alkyl and cycloalkyl group is saturated or unsaturated;

$R^1$ is hydrogen or a $C_{1-6}$ alkyl group that is substituted, saturated or unsaturated, straight or branched;

A is a chromophoric aromatic ring or ring system, and carries 1 to 8 substituents selected from the group consisting of hydrogen, hydroxy, mercapto, amino, acyl, ester, esterified hydroxy group, cyano, nitro; substituted, saturated or unsaturated, straight or branched alkyl, alkoxy, alkylthio, and arylalkoxy groups; substituted or unsubstituted aryl groups, and a polymeric group;

n is 1 or 2; and with the proviso that formula I is not 2-ethoxy-1-phenyl-ethanone.

23. A method according to claim 22 wherein the consumer product is selected from the group consisting of laundry detergents, fabric softeners, fabric softener sheets, cleaning compositions, swimming pool additives, toiletries, and cosmetic products, such as shampoo, conditioners and sunscreens.

24. A method according to claim 22 wherein the precursor is activated to form an organoleptic and/or antimicrobial agent.

25. A method according to claim 24 wherein the precursor is activated by exposure to an activating agent selected from the group consisting of light, heat, hydrolysis, and enzymes.

* * * * *